United States Patent [19]
McGuire et al.

[11] 3,991,608
[45] Nov. 16, 1976

[54] IMPACT SIMULATOR METHOD AND APPARATUS

[75] Inventors: James T. McGuire; Charles R. Plummer; Peter P. Rudowsky, all of Bridgeton, N.J.

[73] Assignee: Owens-Illinois, Inc., Toledo, Ohio

[22] Filed: Oct. 26, 1970

[21] Appl. No.: 83,974

[52] U.S. Cl. ................................................. 73/94
[51] Int. Cl.[2] .......................................... G01N 3/08
[58] Field of Search ............... 73/12, 52, 78, 81, 94; 209/79

[56] References Cited
UNITED STATES PATENTS

| | | | |
|---|---|---|---|
| 2,339,460 | 1/1944 | Cozzoli | 73/12 |
| 2,377,536 | 6/1945 | Wisner | 73/12 X |
| 3,067,605 | 12/1962 | Bliss | 73/12 |
| 3,101,848 | 8/1963 | Uhlig | 209/72 |
| 3,247,596 | 4/1966 | Hintermaier | 73/94 X |
| 3,331,241 | 7/1967 | Boonstra et al. | 73/94 |

*Primary Examiner*—Charles A. Ruehl
*Attorney, Agent, or Firm*—D. T. Innis; E. J. Holler

[57] ABSTRACT

The testing of glass containers for structural defects, principally in the side wall surfaces thereof, is provided wherein bottles are conveyed in succession at spaced-apart intervals through the testing device. The testing device takes the form of a wheel having a substantial thickness mounted to rotate about a vertical axis, with the periphery of the wheel extending over a portion of the width of the conveyor belt. A pressure plate having a vertical surface facing in the direction of the wheel and positioned and supported from the opposite side of the conveyor has a surface configuration closely paralleling that of the curvature of the wheel. The pressure plate and wheel are positioned relative to each other such that a container, in order to pass between the wheel and the pressure plate, is subjected to a lateral compressive force. Because of the contour of the wheel and length of the pressure plate, at least 180° of the bottle circumference finds itself being compressed by the wheel during the precessing motion of the container through the testing device. The force applied by the wheel to the bottle or container is applied by a fluid motor whose output piston acts upon the movable axis of the wheel to bias the wheel in the direction of the pressure plate. Thus it can be seen that every container may be physically stressed and if a defective bottle is present, it will be broken by the compressive force. Both the wheel and pressure plate bottle-engaging surfaces are lined with a plastic material having the characteristic that it does not readily retain glass fragments.

2 Claims, 4 Drawing Figures

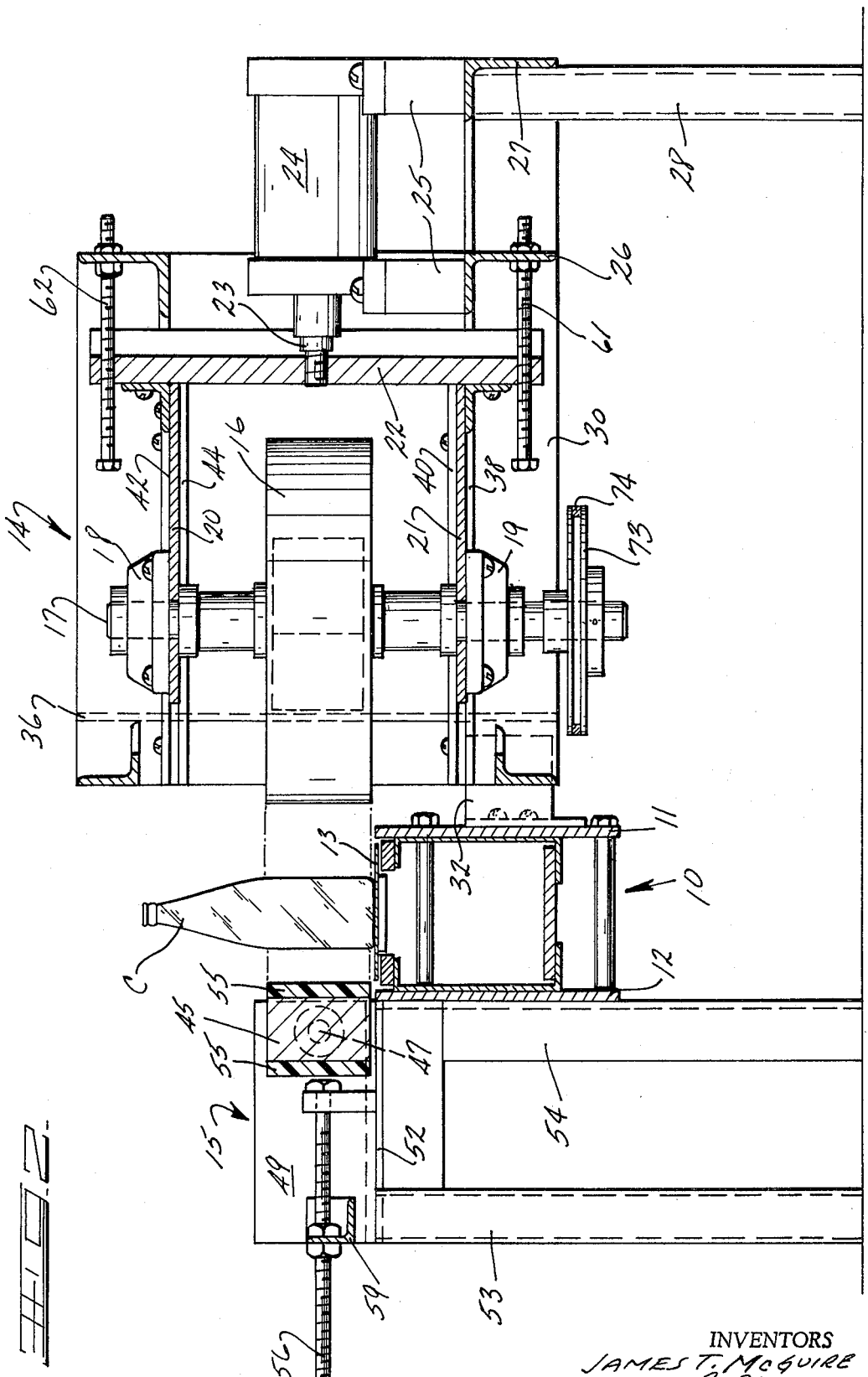

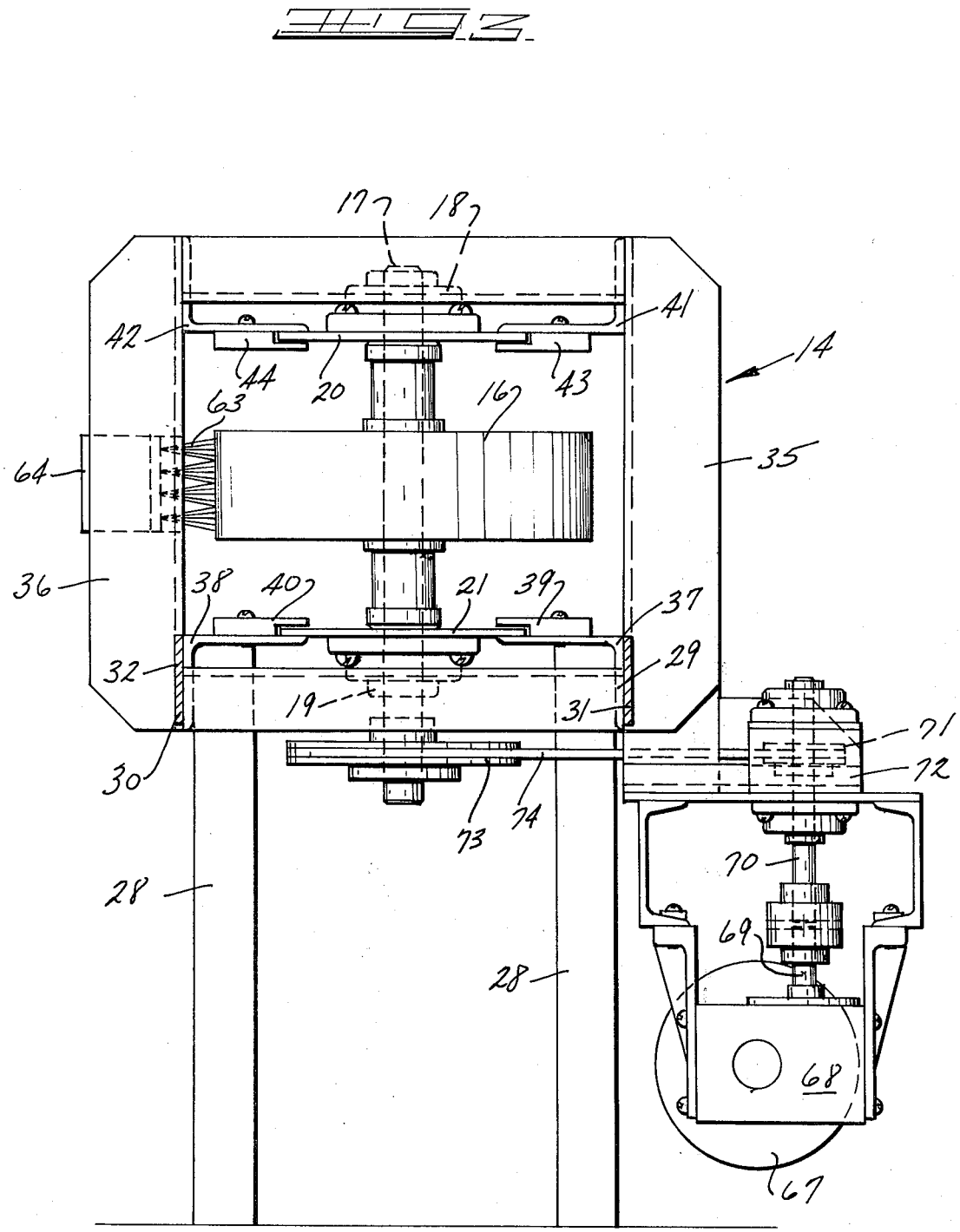

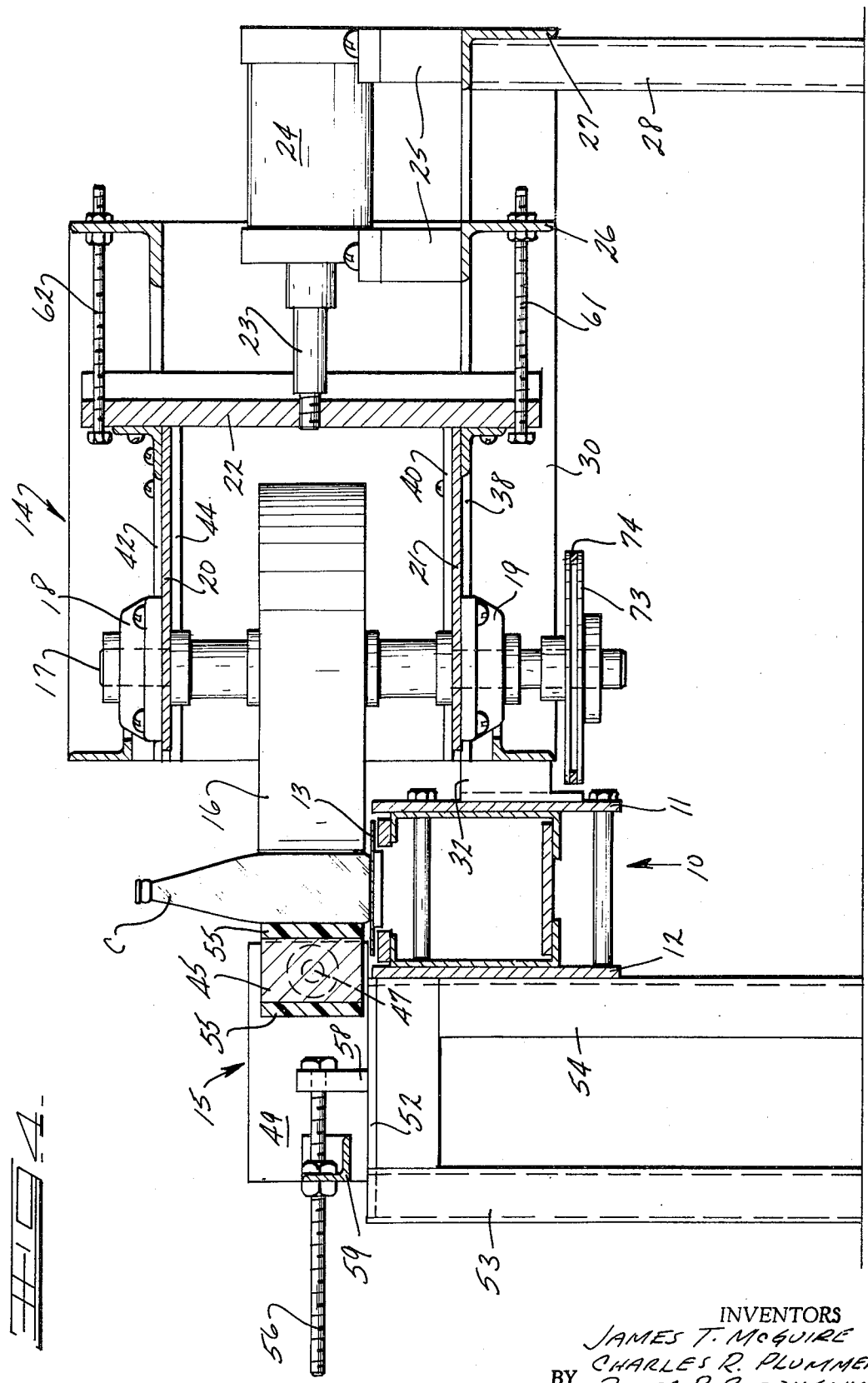

IMPACT SIMULATOR METHOD AND APPARATUS

BACKGROUND OF THE INVENTION

It has been the practice in the past to test glass containers, and in particular containers which are intended to be used for pressure products, such as soft drinks and beer, by inspecting these containers for checks, both in the finish where the sealing of the container by a closure may be affected by the presence of a check and in the heel of the container which is the load and abuse bearing surface of the container. The presence of a check might result in a structural failure in the container when filled with a product under pressure. The side walls of the containers have, by and large, been inspected only by visual observation by selectors observing the containers as they move in succession past a diffuse light source. The selectors are capable of selecting out those containers which have gross defects and in some instances will be able to segregate containers having other, more obvious, defects such as checks, seeds and blisters. It has also been proposed in the past to check the structural strength of containers by subjecting them to an internal pressure test or, as is commonly known, a "bursting strength test". The "bursting strength test", however, normally is a test conducted on statistical samples of containers which are stressed by internal pressure to the point of failure and to the present time has not lent itself to being a high-speed production-type test where every container would be subjected to a specific internal pressure.

Applicants have found that by subjecting containers to a radial loading on the side wall, that those containers which have structural defects in the walls thereof or have insufficient strength to withstand a specific load, will be broken and thus effectively selected out of a line of ware being produced.

DESCRIPTION OF PRIOR ART

An example of an internal pressure testing procedure and apparatus is disclosed in U.S. Pat. No. 3,010,310 issued Nov. 28, 1961. This apparatus has not found wide acceptance in the glass container industry, principally because of its inability to operate trouble-free for extended periods of time and at relatively high speed.

SUMMARY OF THE INVENTION

This invention relates to a method and apparatus for testing glass containers for structural defects wherein the containers are moved in succession along a generally straight path. Intermediate this path, a wheel mounted for rotation about its vertical axis is driven at a preselected circumferential velocity. The periphery of the wheel engages containers which are moving in said path, and in conjunction with an elongated pressure plate mounted in opposing relationship to the portion of the wheel which extends over the conveyor, a compressive force is applied to the container while confined between the wheel and the pressure plate so as to apply a compressive load to the containers throughout a substantially complete circumference of the container.

BRIEF DESCRIPTION OF THE DRAWINGS

FIG. 2 is a vertical, cross-sectional view taken generally at line 2—2 of FIG. 1;

FIG. 3 is a vertical, cross-sectional view takn at line 3—3 of FIG. 1; and

FIG. 4 is a sectional view, similar to FIG. 2, showing the position of the wheel and pressure plate in operative position in relation to a container being tested.

Figure 1:
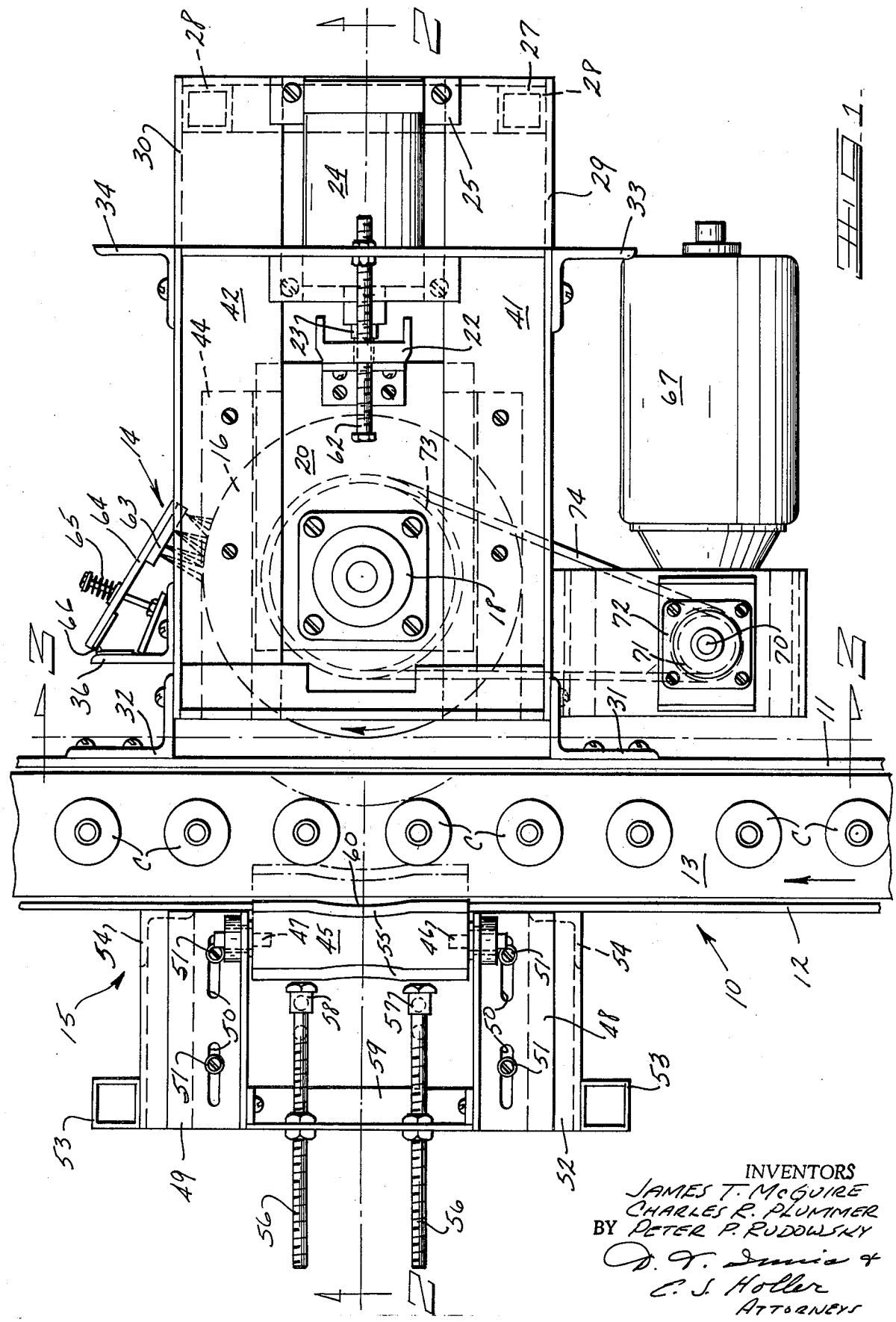
FIG. 1 is a top plan view of the testing apparatus of the invention.

With particular reference to the drawings, a conveyor, generally designated 10, formed of the usual side frame members 11 and 12, serves to support a moving belt 13.

As can best be seen in FIG. 1, the belt 13 is moving in the direction of the arrow shown thereon.

Containers "C" to be inspected are positioned upright on the conveyor belt 13 at spaced intervals and are conveyed by the belt through the testing apparatus to be described in detail below.

Basically, the testing device takes the form of a force-applying wheel portion, generally designated 14, which is mounted to the right side of the conveyor 10, as viewed in FIG. 1, and a pressure plate portion, generally designated 15, mounted on the left-hand side of the conveyor, as viewed in FIGS. 1, 2 and 4.

The wheel supporting portion of the testing apparatus is composed of a wheel 16 supported by a vertical shaft 17. The shaft 17 is keyed to the wheel 16 and the upper and lower ends of the shaft 17 extend through thrust bearings 18 and 19. The thrust bearing 18 is bolted to a generally horizontal plate 20 and the thrust bearing 19 is bolted to the underside of a horizontal plate 21. The plates 20 and 21 are maintained in their spaced-apart relationship and joined together by a vertically extending bar 22. The plates 20 and 21, which serve to support the thrust bearings for the wheel support shaft 17, may be shifted or biased relative to the conveyor by the application of a force to the bar 22.

As shown in FIGS. 2 and 4, the bar 22 has connected thereto, midway of its vertical height, an output shaft 23 of a fluid motor 24. The fluid motor 24 is mounted on a pair of supporting blocks 25. The blocks 25 in turn are supported by angle irons 26 and 27 serving as part of the main supporting frame for the wheel portion of the testing device.

With particular reference to FIGS. 1, 3 and 4, the angle iron 27 is shown as being supported by a pair of vertically extending legs 28. A pair of side frame members 29 and 30 are joined to the angle iron 27 and legs 28 at the rearward end and at their forward ends are bolted to the conveyor frame member 11 by angle brackets 31 and 32. A pair of vertically extending angle iron membrers 33 and 34 adjacent the rearward end of the wheel supporting structure along with similar vertically extending angle iron members 35 and 36 adjacent the forward end of the wheel supporting structure, in effect, provide supporting members for the upper and lower rectangular frame members.

As previously stated, the plates 20 and 21 are shiftable or movable by the motor 24 or by hand in the initial setting up of the wheel position relative to the containers to be tested. The lower plate 21 has its lateral edges supported by a pair of spaced, underlying angle brackets 37 and 38.

A pair of retaining brackets 39 and 40 are mounted on the angle brackets 37 and 38 and are elongated and have portions thereof which overlie the plate 21. Thus it can be seen that the brackets 37 and 39 together form a slideway for the right-hand side of the plate 21, as viewed in FIG. 3, and the brackets 38 and 40 together form a slideway or guideway for the left-hand side of the plate 21.

In a like manner, a pair of angle brackets 41 and 42 overlie the opposite edges of the plate 20 and retaining brackets 43 and 44 bolted to the underside of the brackets 41 and 42 together serve as slideways or guideways for the plate 20. Thus it can be seen, when viewing FIG. 1, that the plates 20 and 21 and the wheel 16 may be shifted as a unit, from the position shown in FIG. 1 in full line to the dotted line position, wherein overlies a portion of the conveyor 13 and the periphery of the wheel will engage containers "C" moving along the conveyor.

FIGS. 1–3 show the wheel in its retracted position, while FIG. 4 specifically illustrates the wheel in its operative or testing position. In actual practice, the fluid motor 24 is functionally provided as a means for biasing the wheel 16 in the conveyor direction rather than serving specifically as a means for shifting the wheel bodily over the entire distance between fully retracted and ware-engaging positions. The plates 20 and 21 and the wheel are shifted manually to a preselected position depending upon the ware diameter and position of the pressure plate and the motor 24 then, when pressurized, will provide the biasing force for testing purposes.

The pressure plate portion 15 of the testing apparatus is composed of an elongated block 45, generally in rectangular form, with its ends supported by pivot pins 46 and 47. The pins 46 and 47 extend through openings provided in the vertical portion of a pair of angle brackets 48 and 49. The horizontal portions of the angle brackets 48 and 49 are provided with elongated slots 50, as best shown in FIG. 1, through which extend threaded bolts 51. The bolts 51 are threaded into a base plate 52. The base plate 52 is supported at approximately the height of the conveyor belt 13 by a pair of legs 53. A second pair of legs 54 in the form of angle irons support the forward or conveyor fronting end of the plate 52 and are also joined to the frame member 12 of the conveyor, it being understood that the pair of legs 54 also serve, to a certain extent, as supports for the conveyor itself, as well as supporting the pressure plate portion of the testing device.

It can readily be seen that through the horizontal adjustability of the brackets 48 and 49, that the block 45 may be shifted to a position overlying a portion of the conveyor, as shown in phantom line in FIG. 1 and full line in FIG. 4. The block 45 is faced with a plastic material 55, so as to present to the bottle being tested a surface which compresses to a limited extent and is not abrasive to the glass container. Likewise, the peripheral surface of the wheel 16 is faced with a similar plastic material, for example polyurethane, which is of a thickness so that it is compressible to a limited extent and has the attribute of not becoming imbedded with broken fragments of glass. The pressure plate or block 45 is adjustable relative to the conveyor surface by threaded bolts 56 which extend through a pair of mounting blocks 57 and 58 which are fixed to the base plate 52 and threaded nuts on either side of a bracket-connecting member 59.

It should be pointed out that the conveyor fronting portion or body-engaging portion of the block 45 is provided with an arcuate contour at 60. This contour 60 closely parallels the contour of the wheel 16 when in position to engage containers. In other words, the arc 60 has substantially the same center as the wheel 16.

The block 45 is of a length such that a container being tested will be compressed between the block and the wheel through at least 180° of the bottle circumference. Thus, with the wheel 16 turning in the direction of the arrow shown in FIG. 1, the containers, as they are confined between the moving wheel and the block 45, will rotate in a counterclockwise direction when viewed from above, and the containers will be compression loaded at those portions which are in contact with the wheel and block, while those portions of the container that are displaced 90° from these contact points, will be placed under tension. As the bottles or containers pass through the testing area, the entire circumference of the container will be alternately subjected to compression forces and tension forces. The wheel is, as previously indicated, biased in the direction of the block 45 by the motor 24.

The bar 22, which connects the plates 20 and 21 together, has its upper and lower ends guided by a pair of bolts 61 and 62. These bolts serve a function which perhaps is best explained when viewing FIG. 4, wherein it can be seen that the bar 22 is positioned to the left to the extent necessary to stress the container "C"; however, the bar 22 does not engage the heads of the bolts 61 and 62. This amount of play is necessary so that the motor 24 may be applying a preselected force to the wheel 16 regardless of any slight variations in bottle diameter. However, in the event the container is defective and as a result of the induced stresses in the container the container breaks, then the wheel 16 would obviously move to the left, as viewed in FIG. 4. The heads of the bolts 61 and 62 serve as limit stops to prevent the wheel and its support from moving to any considerable degree and as a subsequent container enters the area between the wheel and the block 45, the wheel will move back to the position shown in FIG. 4, yet the force applied will still be that determined by the amount of pressure introduced to the motor 24. In the event a container breaks and glass fragments become loosely adhered to the surface of the wheel, a brush 63, mounted to the end of a pivoted arm 64, will remove any glass fragments from the surface of the wheel and the wheel surface that contacts the subsequent containers will be clean.

As can be seen in FIG. 1, the brush 63 and its supporting arm 64 are biased in the direction of the wheel 16 by a compression spring 65, with the arm 64 being pivoted to the angle iron member 36 by a hinge 66.

As previously explained, the wheel 16 is rotated and this is accomplished by a motor 67 connected to a gear box 68 having an output shaft 69 extending vertically upward, with the output shaft coupled to a drive shaft 70. The drive shaft 70 is connected to a pulley 71 carried in a bearing housing 72. The lower end of the shaft 17, which supports the wheel 16, extends through the lower thrust bearing 19 and has a pulley 73 fixed thereto. A drive belt 74 extends around the pulleys 73 and 71. Thus it can be seen that the motor 67, through the gear box or transmission 68, drives the pulley 71 which in turn, through the belt 74, drives the pulley 73 connected to the shaft 17 of the wheel 16.

It should be noted from FIG. 1, that the axes of the shafts 17 and 70 are positioned such that repositioning of the wheel 16 in relation to the conveyor 13 will not appreciably change the relative distance between the shafts 70 and 17 so that lateral movement of the shaft 17 relative to the shaft 70 will not affect the belt drive, nor present any unknown or unpredictable forces on the wheel 16.

The pressure block 45, since it is supported by pivot pins 46 and 47, can pivot about a horizontal axis to a limited extent, thus accommodating itself to containers whose side walls are not perfectly cylindrical. Furthermore, the block has the same contour 60 on its opposed surface so that the block is, in effect, reversible.

With the particular apparatus disclosed, it can be seen that containers moving in series through the zone between the wheel and pressure block will be stressed and the defective containers will be broken, with the broken glass being conveyed away from the testing zone.

While the foregoing description has been directed to the specific apparatus disclosed in detail in the drawings, it should be kept in mind that the application of force to a container while the container is moving in a substantially straight line between the confining members, namely the wheel and pressure block, could be accomplished by the use of a moving belt biased against the container by a supporting member similar to that used for the wheel. With such an arrangement the pressure block would have a generally planar face engaging the container, with the belt being supported and moving parallel to the conveyor.

We claim:

1. Apparatus for testing glass containers for structural defects comprising, conveyor means for moving containers in an upright position in series in spaced-apart relationship, endless bottle-engaging means mounted adjacent said conveyor for movement in a vertical plane parallel to the direction of movement of said conveyor, means for continuously moving said bottle-engaging means at a preselected velocity, said bottle-engaging means having a substantial vertical height with a portion of said bottle-engaging means extendng over a portion of said conveyor, an elongated pressure plate mounted in opposing relationship to that portion of said bottle-engaging means extending over the conveyor, means for mounting said pressure plate for slight pivotal movement about a horizontal axis, parallel to said conveyor, force applying means for biasing said bottle-engaging means and said pressure plate toward each other whereby containers moving along said conveyor are engaged between said bottle-engaging means and pressure plate to thereby be stressed.

2. The apparatus as defined in claim 1 wherein said means for mounting said pressure plate is adjustable towards and away from the conveyor.

* * * * *